(12) United States Patent
Schwager et al.

(10) Patent No.: US 9,339,315 B2
(45) Date of Patent: May 17, 2016

(54) BONE FIXATION SYSTEM WITH CURVED PROFILE THREADS

(71) Applicant: Stryker European Holdings I, LLC, Kalamazoo, MI (US)

(72) Inventors: Manuel Schwager, Zurich (CH); Rene Wirth, Lommiswil (CH); Axel Cremer, Lommiswil (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/640,630

(22) Filed: Mar. 6, 2015

(65) Prior Publication Data
US 2015/0182270 A1    Jul. 2, 2015

Related U.S. Application Data

(63) Continuation of application No. 12/719,316, filed on Mar. 8, 2010, now abandoned.

(51) Int. Cl.
*A61B 17/04* (2006.01)
*A61B 17/86* (2006.01)
*A61F 2/08* (2006.01)

(52) U.S. Cl.
CPC .............. *A61B 17/863* (2013.01); *A61B 17/86* (2013.01)

(58) Field of Classification Search
CPC .. A61B 17/86; A61B 17/8605; A61B 17/862; A61B 17/8625; A61B 17/861; A61B 17/8615
USPC ............................ 606/300–321; 411/399, 411
See application file for complete search history.

(56) References Cited

U.S. PATENT DOCUMENTS

| | | |
|---|---|---|
| 3,394,626 A | 7/1968 | Oliver |
| 3,495,494 A | 2/1970 | Scott |
| 3,741,205 A | 6/1973 | Markolf et al. |
| 4,878,791 A * | 11/1989 | Kurihara et al. ............... 411/55 |
| 5,151,103 A | 9/1992 | Tepic et al. |
| 5,156,616 A | 10/1992 | Meadows et al. |
| 5,275,601 A | 1/1994 | Gogolewski et al. |
| 5,423,826 A | 6/1995 | Coates et al. |
| 5,607,428 A | 3/1997 | Lin |
| 5,709,686 A | 1/1998 | Talos et al. |

(Continued)

FOREIGN PATENT DOCUMENTS

| | | |
|---|---|---|
| CA | 2367085 A1 | 9/2000 |
| CA | 2408327 A1 | 3/2001 |

(Continued)

OTHER PUBLICATIONS

Koval et al., Journal of Orthopedic Trauma, vol. 11, No. 7, pp. 521-524, 1997.

(Continued)

*Primary Examiner* — Kevin T Truong
*Assistant Examiner* — Si Ming Ku
(74) *Attorney, Agent, or Firm* — Lerner, David, Littenberg, Krumholz & Mentlik, LLP

(57) ABSTRACT

A bone fastener for use in orthopedic surgery for fixing an implant to bone has a threaded or unthreaded shaft configured to engage bone and a head having a thread on an outer surface to engage the implant. The thread on the head of the fastener has a profile in cross section that includes peaks with a curved shape.

19 Claims, 7 Drawing Sheets

(56) References Cited

U.S. PATENT DOCUMENTS

| | | |
|---|---|---|
| 6,030,162 A * | 2/2000 | Huebner .................. 411/413 |
| 6,030,389 A | 2/2000 | Wagner et al. |
| 6,129,728 A | 10/2000 | Schumacher et al. |
| 6,129,730 A | 10/2000 | Bono et al. |
| 6,162,001 A | 12/2000 | Goodwin et al. |
| 6,206,881 B1 | 3/2001 | Frigg et al. |
| 6,273,889 B1 | 8/2001 | Richelsoph |
| 6,315,564 B1 | 11/2001 | Levisman |
| 6,364,882 B1 | 4/2002 | Orbay |
| 6,669,701 B2 | 12/2003 | Steiner et al. |
| 6,726,689 B2 | 4/2004 | Jackson |
| 6,730,091 B1 | 5/2004 | Pfefferle et al. |
| 6,786,909 B1 | 9/2004 | Dransfeld et al. |
| 6,821,278 B2 * | 11/2004 | Frigg et al. .................. 606/291 |
| 7,063,701 B2 * | 6/2006 | Michelson .................. 606/307 |
| 7,179,260 B2 | 2/2007 | Gerlach et al. |
| 2001/0014807 A1 | 8/2001 | Wagner et al. |
| 2002/0058940 A1 | 5/2002 | Frigg et al. |
| 2002/0183752 A1 | 12/2002 | Steiner et al. |
| 2003/0153919 A1 | 8/2003 | Harris |
| 2003/0171754 A1 | 9/2003 | Del Medico |
| 2004/0073218 A1 | 4/2004 | Dahners |
| 2004/0167524 A1 | 8/2004 | Jackson |
| 2004/0181226 A1 | 9/2004 | Michelson |
| 2004/0193165 A1 | 9/2004 | Orbay |
| 2004/0193269 A1 | 9/2004 | Fraser et al. |
| 2004/0260292 A1 | 12/2004 | Orbay et al. |
| 2005/0010226 A1 | 1/2005 | Grady et al. |
| 2005/0015089 A1 | 1/2005 | Young et al. |
| 2005/0059970 A1 | 3/2005 | Kolb |
| 2005/0065524 A1 | 3/2005 | Orbay |
| 2005/0070904 A1 | 3/2005 | Gerlach et al. |
| 2005/0143742 A1 | 6/2005 | Porcher |
| 2005/0165395 A1 | 7/2005 | Orbay et al. |
| 2005/0165400 A1 | 7/2005 | Fernandez |
| 2005/0192578 A1 | 9/2005 | Horst |
| 2005/0192580 A1 | 9/2005 | Dalton |
| 2005/0240186 A1 | 10/2005 | Orbay |
| 2005/0245931 A1 | 11/2005 | Orbay |
| 2005/0261688 A1 | 11/2005 | Grady et al. |
| 2005/0273105 A1 | 12/2005 | Konieczynski et al. |
| 2005/0277937 A1 | 12/2005 | Leung et al. |
| 2006/0004361 A1 | 1/2006 | Hayeck et al. |
| 2006/0004362 A1 | 1/2006 | Patterson et al. |
| 2006/0009771 A1 | 1/2006 | Orbay et al. |
| 2006/0058796 A1 | 3/2006 | Hartdegen et al. |
| 2006/0058797 A1 | 3/2006 | Mathieu et al. |
| 2006/0116678 A1 | 6/2006 | Impellizzeri |
| 2006/0142766 A1 | 6/2006 | Schafer |
| 2006/0149251 A1 | 7/2006 | Ziolo et al. |
| 2006/0149257 A1 | 7/2006 | Orbay et al. |
| 2006/0149264 A1 | 7/2006 | Castaneda et al. |
| 2006/0195085 A1 | 8/2006 | Happonen et al. |
| 2006/0195104 A1 | 8/2006 | Schlafli et al. |
| 2006/0217722 A1 | 9/2006 | Dutoit et al. |
| 2006/0229619 A1 | 10/2006 | Orbay et al. |
| 2006/0235399 A1 | 10/2006 | Carls et al. |
| 2006/0235400 A1 | 10/2006 | Schneider |
| 2006/0263171 A1 | 11/2006 | Schwarz |
| 2006/0264947 A1 | 11/2006 | Orbay et al. |
| 2006/0276793 A1 | 12/2006 | Berry |
| 2007/0083207 A1 | 4/2007 | Ziolo et al. |
| 2007/0088360 A1 | 4/2007 | Orbay et al. |
| 2007/0093835 A1 | 4/2007 | Orbay et al. |
| 2007/0276383 A1 | 11/2007 | Rayhack |
| 2007/0276386 A1 | 11/2007 | Gerlach et al. |
| 2008/0021477 A1 | 1/2008 | Strnad et al. |
| 2008/0058815 A1 * | 3/2008 | Young .................. 606/69 |
| 2008/0086136 A1 | 4/2008 | Bednar |
| 2008/0089759 A1 | 4/2008 | Diekmeyer |
| 2008/0213065 A1 | 9/2008 | Sussenbach |
| 2008/0234750 A1 | 9/2008 | Woods et al. |
| 2008/0234751 A1 | 9/2008 | McClintock |
| 2008/0234752 A1 | 9/2008 | Dahners |
| 2008/0234757 A1 | 9/2008 | Jacofsky et al. |
| 2008/0288000 A1 | 11/2008 | Cawley |
| 2009/0036933 A1 | 2/2009 | Dube et al. |
| 2009/0076553 A1 | 3/2009 | Wolter |
| 2009/0088807 A1 | 4/2009 | Castaneda et al. |
| 2009/0118773 A1 | 5/2009 | James et al. |
| 2009/0192550 A1 | 7/2009 | Leung et al. |

FOREIGN PATENT DOCUMENTS

| | | |
|---|---|---|
| CA | 2405053 A1 | 10/2001 |
| CA | 2601482 A1 | 7/2008 |
| CN | 1373646 A | 10/2002 |
| DE | 4341980 A1 | 6/1995 |
| DE | 4343117 A1 | 6/1995 |
| DE | 19858889 A1 | 6/2000 |
| DE | 10356904 A1 | 9/2005 |
| DE | 102004035546 A1 | 2/2006 |
| DE | 102005015496 A1 | 11/2006 |
| EP | 0230678 A1 | 8/1987 |
| EP | 0486762 A1 | 5/1992 |
| EP | 0 705 572 A2 | 4/1996 |
| EP | 1112722 A2 | 7/2001 |
| EP | 1158916 A1 | 12/2001 |
| EP | 1250892 A2 | 10/2002 |
| EP | 1364623 A1 | 11/2003 |
| EP | 1468655 A2 | 10/2004 |
| EP | 1649819 A1 | 4/2006 |
| EP | 1674041 A1 | 6/2006 |
| EP | 1779797 A2 | 5/2007 |
| EP | 1878394 A2 | 1/2008 |
| EP | 1987792 A1 | 11/2008 |
| EP | 2016918 A1 | 1/2009 |
| FR | 2701386 A1 | 8/1994 |
| FR | 2760628 A1 | 9/1998 |
| GB | 2345108 A | 6/2000 |
| GB | 2406056 A | 3/2005 |
| WO | 9300518 A1 | 1/1993 |
| WO | 9515727 A1 | 6/1995 |
| WO | 9955248 A1 | 11/1999 |
| WO | 0066012 A1 | 11/2000 |
| WO | 0119264 A2 | 3/2001 |
| WO | 0119267 | 3/2001 |
| WO | 2004086990 A1 | 10/2004 |
| WO | 2004089233 A1 | 10/2004 |
| WO | 2004098442 A1 | 11/2004 |
| WO | 2004103193 A1 | 12/2004 |
| WO | 2005037114 A1 | 4/2005 |
| WO | 2005044122 A1 | 5/2005 |
| WO | 2006029274 A1 | 3/2006 |
| WO | 2006037898 A1 | 4/2006 |
| WO | 2006072284 A1 | 7/2006 |
| WO | 2006072379 A1 | 7/2006 |
| WO | 2006074792 A2 | 7/2006 |
| WO | 2007108734 A1 | 9/2007 |
| WO | 2007146165 A2 | 12/2007 |
| WO | 2008007194 A2 | 1/2008 |
| WO | 2008007196 A2 | 1/2008 |
| WO | 2008077482 A1 | 7/2008 |
| WO | 2008077491 A1 | 7/2008 |
| WO | 2008077493 A1 | 7/2008 |

OTHER PUBLICATIONS

The Distal Radius Plate and Instrument Set, Synthes, 1995.

Extended European Search Report for Application No. 10002389.4 dated Jul. 29, 2010.

* cited by examiner

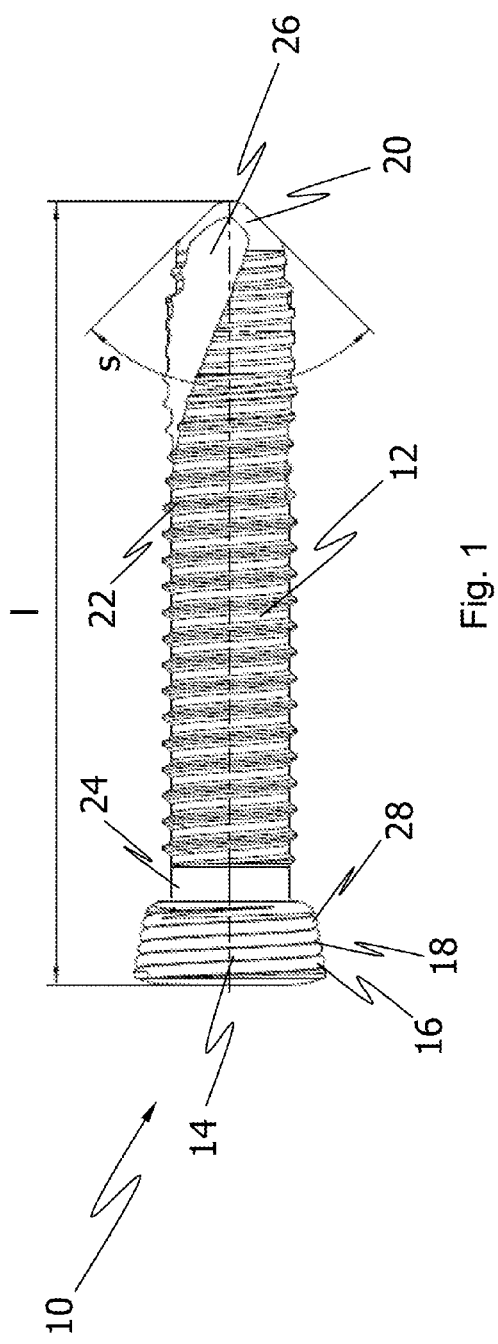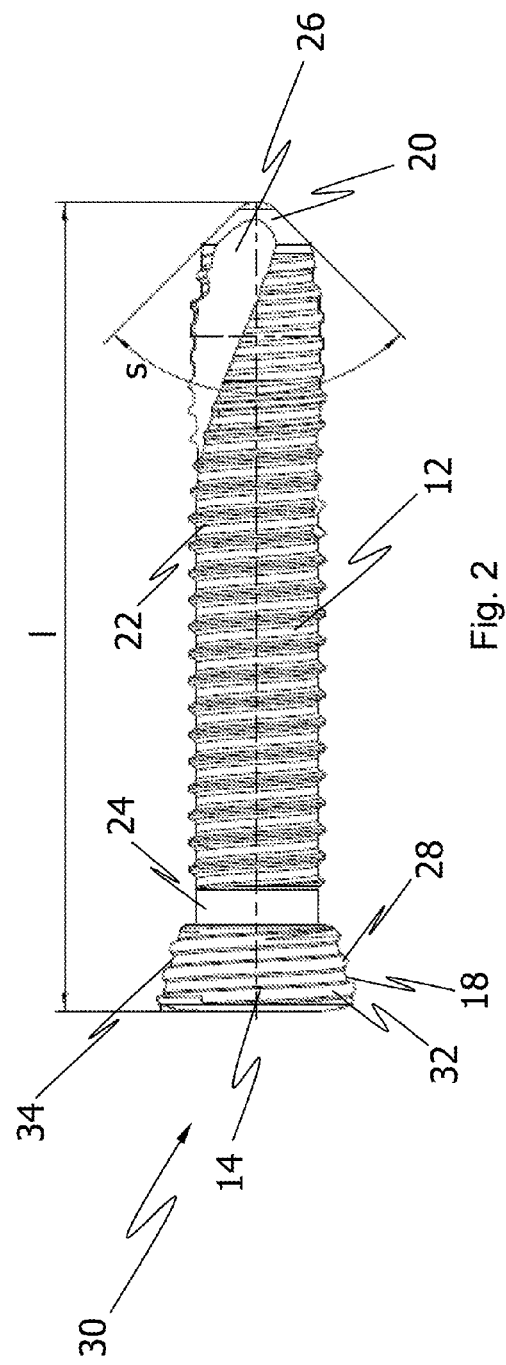

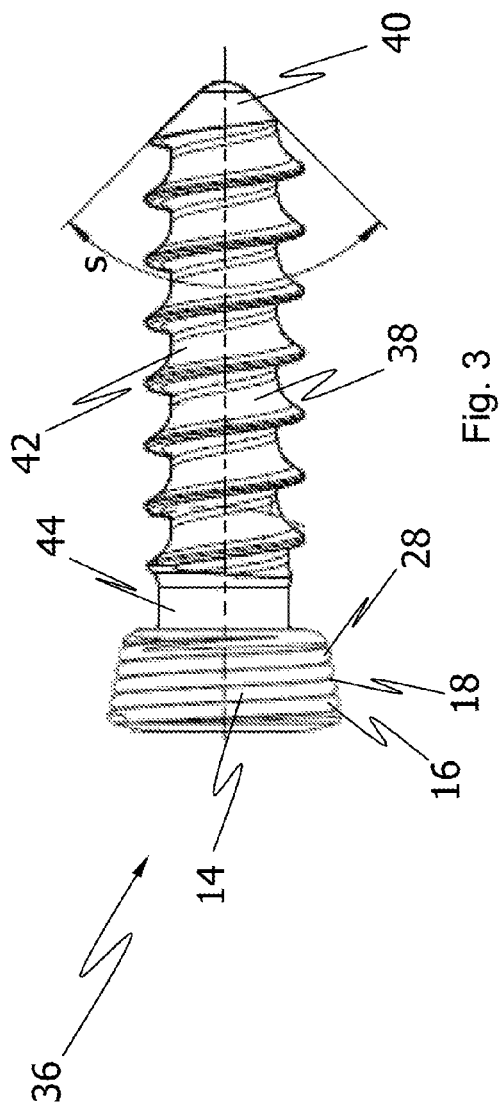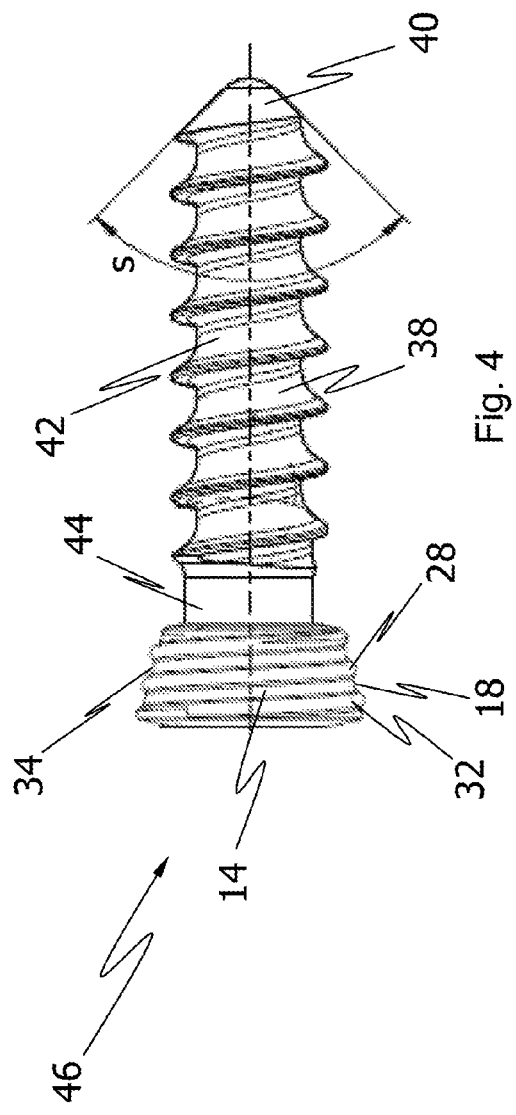

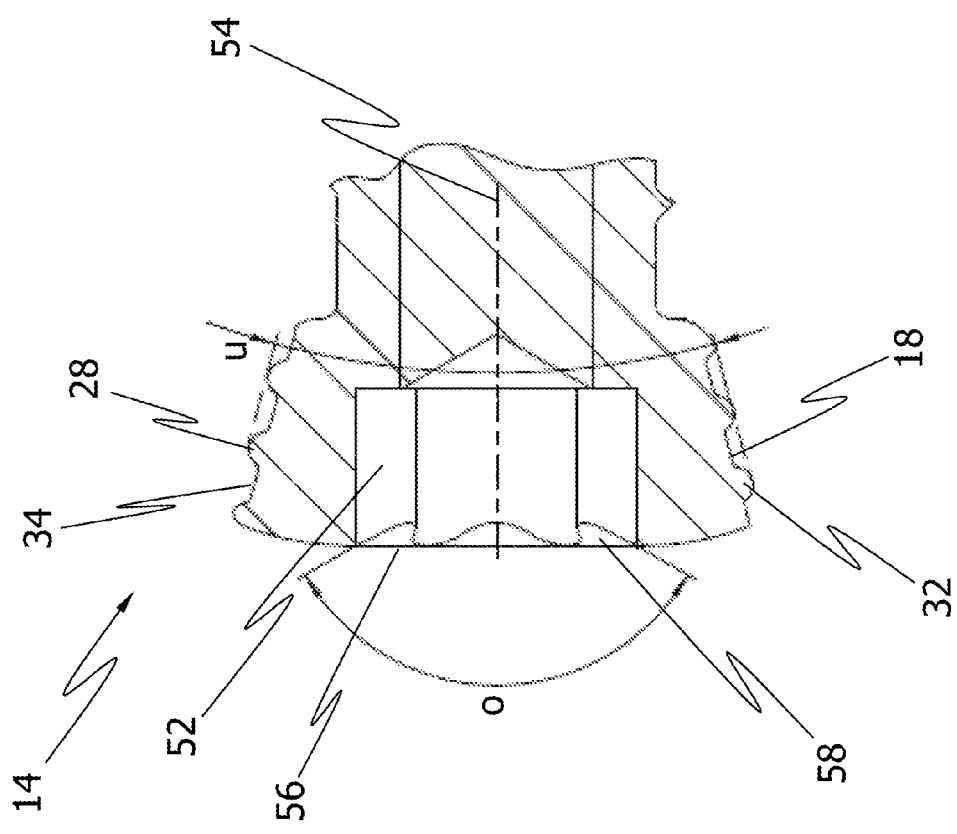
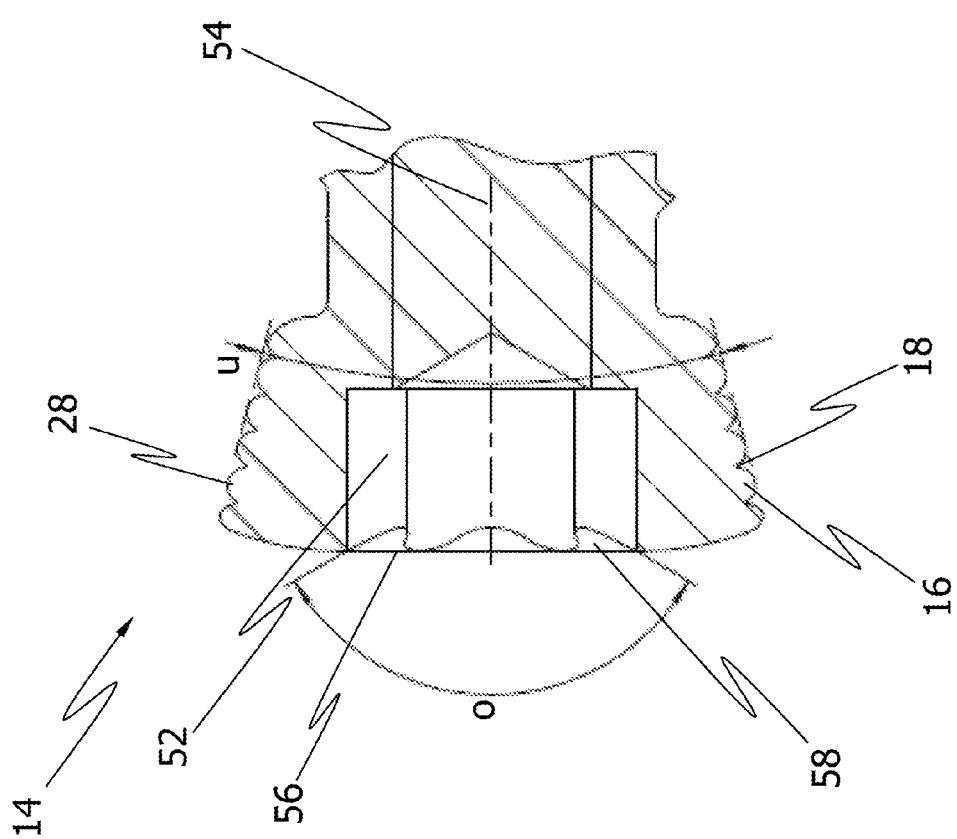

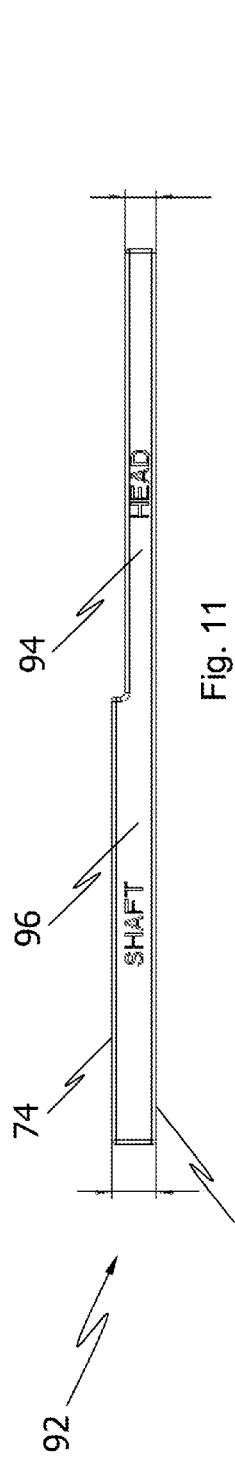
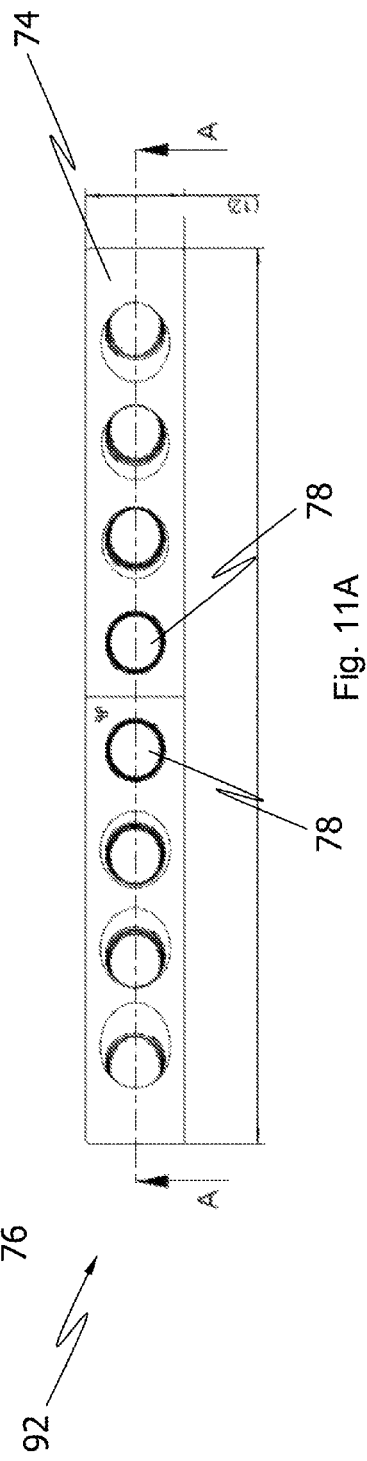
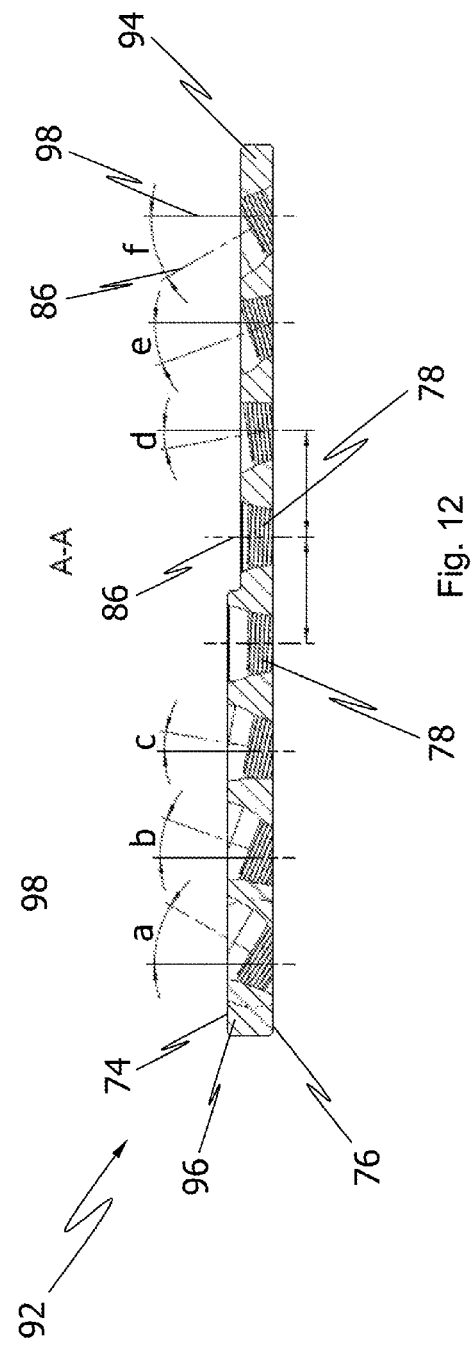

BONE FIXATION SYSTEM WITH CURVED PROFILE THREADS

CROSS-REFERENCE TO RELATED APPLICATIONS

This application is a continuation of U.S. application Ser. No. 12/719,316 filed Mar. 8, 2010 the disclosure of which is incorporated herein by reference.

BACKGROUND OF THE INVENTION

The present disclosure generally relates to a bone fastener such as a bone screw or bone peg for use in orthopedic surgery, preferably for fixing an implant such as a bone plate to bone. The disclosure further relates to an implant system for fixation of bone.

Bone screws are available in a plurality of variations for different applications. Bone screws which can be secured to a bone plate or a similar implant are also known as locking screws. For locking the bone screw to the bone plate, a head of the bone screw is provided with a thread that mates with a corresponding thread on an inner surface of a plate hole.

U.S. Patent Publication Nos. 2005/0277937 and 2009/0192550 relate to a typical locking screw which is intended to be secured to a bone plate. The head of the bone screw has a spherical shape and a thread with V-shaped ridges. The thread of the head is a double lead thread which mates with an internal thread of a plate hole. The ridges of the thread provided in the plate hole have a defined angle relative to the plate, whereby the bone screw is correspondingly fixed to the bone plate at a predetermined angle.

The threaded head of a locking screw may also have a cylindrical or conical shape. U.S. Pat. No. 7,179,260 and U.S. Patent Publication No. 2007/0276386 relate to a bone plate system comprising a locking screw with such a head. The screw head is completely or partially threaded to be received in a threaded plate hole. U.S. Patent Publication No. 2005/0261688 relates to a further bone screw having a conically-tapered and threaded head. The flanks and peaks of the threaded head have a trapezoidal shape for mating with internal threads of a plate hole.

EP 0 230 678 A1 relates to an endosteal screw-implant used in dentistry comprising a shaft and a conical head with a spherically shaped portion. The shaft of the screw has a thread which is cylindrically shaped and rounded on its external edges for fixing the shaft into a jaw bone.

The conventional bone fasteners for locking applications have several drawbacks. During the screwing-in operation of the bone fastener head into the implant, the thread of a head of the fastener can tilt and jam within the threaded portion of the implant hole. Thereby, the flanks and peaks of the threaded head and the threaded hole may get damaged. Moreover, splinters from the bone drilling as well as other materials like parts of human tissue can contaminate the edges and grooves of the threads, whereby the thread of the threaded head and the internal thread of the hole of the implant can jam.

SUMMARY OF THE INVENTION

Aspects of the present disclosure are directed to facilitate an easy screwing-in of a threaded bone fastener head into a bone plate or any other implant without jamming.

According to a first aspect, there is provided a bone fastener for use in orthopedic surgery for fixing an implant to bone, wherein the bone fastener comprises a shaft configured to engage bone and a head having a thread, for example, a helical thread on an outer surface to engage the implant. The thread has a profile in cross section including peaks, wherein the peaks have a curved shape.

Each curved peak of the bone fastener can form an arc segment. The arc segment may be derived from a regular circle or a symmetrically or asymmetrically deformed circle (e.g., from an ellipse). A radius of curvature of the arc segment can be between 0.05 mm and 3.0 mm, in particular between 0.1 mm and 1.0 mm. An angular range of the arc segment can be between 30° and 200°, in particular between 45° and 180°. Independently therefrom, an angle between a plane including the core diameter of the head and a tangent of the arc segment may be between −10° and 90°, in particular between 0° and 50°. Each curved peak of the bone fastener may be defined by a height h which extends from a plane defined by the core of the head to the top of the peak. This height h of the peak can be between 0.1 mm and 3.0 mm, in particular between 0.15 mm and 1.5 mm.

The curved peaks can be provided immediately adjacent to each other. Alternatively, the curved peaks can be separated from each other by valleys. In one possible implementation, the valleys have a planar profile. The valleys can also have a rounded, V-shaped, U-shaped or trapezoidally shaped profile in cross section.

Further, the thread of head can include non-curved (e.g., straight) or curved thread flanks. The flanks may connect the peaks and valleys. Each curved flank may be defined by an arc segment. The flanks may generally have a different curvature (e.g., in the opposite direction and/or of a different curvature radius) than the arc segments defining the peaks.

The thread of the head may be a multiple thread such as a double thread. Moreover, the thread of the head can have a constant thread pitch. The thread pitch of the thread of the head may be between 0.1 mm and 5.0 mm, in particular between 0.25 mm and 3.0 mm. The thread of the head may have a thread depth between 0.1 mm and 3.0 mm, in particular between 0.15 mm and 1.5 mm.

The head can have a length between 1.0 mm and 10 mm and a core diameter between 1.0 mm and 20.0 mm. Further, the head may have an outer diameter between 1.0 mm and 20.0 mm. The head can have a generally conical or curved (e.g., spherical) shape. The head may also be cylindrical. Further, the outer diameter of the head can be the same as or greater than the outer diameter of the shaft.

The shaft of the bone fastener may have a core diameter between 1.0 mm and 20.0 mm. The shaft can be unthreaded or at least partially threaded. Generally, a bone fastener having an at least partially threaded shaft can also be referred to as bone screw, whereas a bone fastener with an unthreaded shaft will be referred to as bone peg. The bone screw can be a self-tapping screw or a self-drilling screw. Alternatively, the shaft may take the form of an un-threaded pin or rod.

The head can have a constant core diameter. Alternatively, the core of the head can have a conical or curved (e.g., spherical) shape. In all cases, an outer diameter of the thread of the head may gradually change in a curved (e.g., spherical) or tapering manner.

According to a further aspect, there is provided an implant system for use in orthopedic surgery for fixation of bone. The implant system comprises an implant having an upper surface and a lower surface, at least one hole extending through the upper surface and lower surface, and at least one bone fastener. The at least one bone fastener comprises a shaft configured to engage bone, and a head having a thread on an outer surface to engage the implant, wherein the thread has a profile in cross section including peaks, wherein the peaks have a curved shape.

Due to the rounded shape of the peaks of the thread of the head of the bone fastener, the engagement of the thread in a hole of the implant is improved. Further, tilting and jamming is avoided during the screwing-in operation of the threaded bone fastener head into the implant.

In the aspect described above, the at least one plate hole may include an at least partially threaded portion configured to mate with the thread of the head of the at least one bone fastener. Alternatively, a thread in the plate hole may be formed by the thread of the screw thread engaging the plate hole as generally described in DE 43 43 117 A. In both cases, the parameters of the thread provided in the hole can be similar or identical to the parameters of the thread of the head of the bone fastener as defined herein. In particular, the thread of the hole may have a profile in cross section including peaks and valleys, wherein the peaks and/or valleys have a curved shape.

The at least one hole can include an unthreaded upper portion and a lower threaded portion configured to mate with the thread of the head of the at least one bone fastener. In this case, the upper portion of the at least one hole can have an inward taper with a conical or curved (e.g., spherical) shape.

The threaded portion of the at least one hole can taper towards the lower surface of the implant. Moreover, the threaded portion of the at least one hole can have a multiple thread (e.g., a double thread).

The at least one hole can have a central axis which can be oblique relative to a vertical axis of the implant. An angle defined between the central axis and the vertical axis can be between 0° and 60°. Alternatively, the at least one hole may be oblique relative to the upper surface or lower surface of the implant.

BRIEF DESCRIPTION OF THE DRAWINGS

These and other features, aspects and advantageous of the present disclosure will become apparent from the following detailed description taken in conjunction with the accompanying drawings, wherein:

FIG. 1 is a side view of a first bone fastener embodiment;

FIG. 2 is a side view of a second bone fastener embodiment;

FIG. 3 is a side view of a third bone fastener embodiment;

FIG. 4 is a side view of a fourth bone fastener embodiment;

FIG. 6 is a cross-sectional view of the screw head shown in FIGS. 1 and 3;

FIG. 7 is a cross-sectional view of a screw head shown in FIGS. 2 and 4;

FIG. 11 is a side view of another dummy implant embodiment;

FIG. 11A is a top view of the plate of FIG. 11 and;

FIG. 12 is a cross-sectional view of the implant shown in FIG. 11.

DETAILED DESCRIPTION

Figure 5:
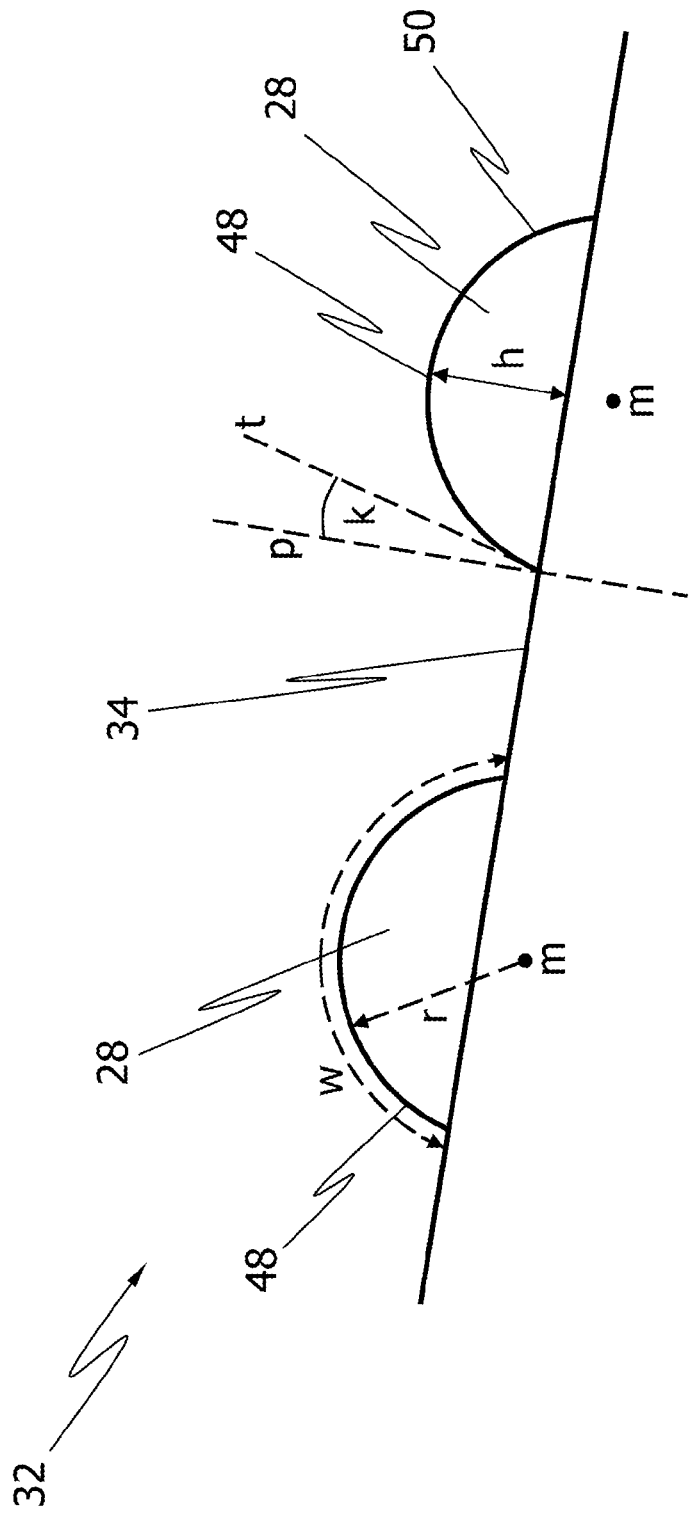
FIG. 5 is a detailed view of peaks of the thread of the bone fastener head shown in FIGS. 2 and 4.

Referring to FIG. 1 shown, there is shows a side view of a first embodiment of a bone fastener in the form of a bone screw 10 for use as a locking screw in orthopedic surgery for fixing an implant (not shown in FIG. 1) to bone. The bone screw 10 comprises a shaft 12 configured to engage bone and a head 14 having a thread 16 on an outer surface 18 to engage the implant. The bone screw 10 has a length 1 between 10 mm and 300 mm. The head 14 is provided at a distal side of the shaft 12 and a tip 20 is provided at a proximal side of the shaft 12. The tip 20 is formed as a cone having an opening angle s of typically 60° to 120°. In the present embodiment the angle s is approximately 90°.

Further, as illustrated in FIG. 1, the shaft has a threaded portion 22. Trapezoidally shaped peaks of the threaded portion 22 are separated by valleys having a planar profile in cross section. The threaded portion 22 of the shaft has a constant thread pitch. The threaded portion 22 extends from the tip 20 to a non-threaded portion 24 adjacent the head end of shaft 12.

The thread of the threaded portion 22 of the shaft 12 is formed as a conventional self-tapping thread, wherein two helically winding cutting grooves 26 are provided at the proximal end of the shaft 12 near the tip 20 for feeding material away. In this cutting area, the shaft 12 has a greater core diameter. However, the outer diameter of the thread of the threaded portion 22 is constant along the whole length of threaded portion 22 in axial direction of the bone screw 10. Thereby, the force during screwing-in the bone screw 10 into bone is reduced.

As shown in FIG. 1, the head 14 of bone screw 10 is adjacent to the non-threaded portion 24 of shaft 12, and the core diameter of the head 14 is greater than the core diameter of the shaft 12. Further, the core of the screw head 14 has a conical shape and an outer diameter of the thread 16 of the head 14 gradually tapers inwardly toward the non-threaded portion 24 of bone screw 10. The thread 16 may be a multiple thread in the form of a double thread (i.e., a double-lead thread).

As also illustrated in FIG. 1, the thread 16 of the screw head 14 has a profile in cross section including peaks 28 provided immediately adjacent to each other. Each of the peaks 28 has a curved shape defined by an arc segment derived from a circle. A radius of curvature of the arc segment amounts to 0.25 mm and an angular range of the arc segment is 78°. The thread 16 of the head 14 also has a constant thread pitch of approximately 1 mm.

FIG. 2 illustrates in a side view another embodiment of a bone screw 30 having a shaft 12 to engage bone and a head 14 to engage an implant. The difference between the bone screw 10 shown in FIG. 1 and the screw 30 shown in FIG. 2 is that the thread 32 is a single-lead thread with the curved peaks 28 of the thread 32 being separated from each other by valleys 34 having a planar profile in cross section. The single thread 32 of the head 14 has the same pitch as each individual thread of the double thread 16 of the screw head shown in FIG. 1. Moreover, the head 14 again has a conical shape. The shaft 12 of the bone screw 30 is formed in the same manner as the shaft of the bone screw 10 shown in FIG. 1. As can be seen in FIGS. 1 and 2, the thread of the bone screw head 14 can extend along the entire length of the head in the axial direction of the screw.

FIG. 3 shows a side view of a bone screw 36 according to another embodiment. The bone screw 36 is essentially a combination of the screw head 14 having the thread configuration of thread 16 shown in FIG. 1 and a modified shaft 38. The shaft 38 of bone screw 36 comprises a tip 40 at its proximal end, a threaded portion 42 and a non-threaded portion 44. The non-threaded portion 44 is provided adjacent the head end of shaft 38 and is adjacent to screw head 14, and the threaded portion 42 extends from the non-threaded portion 44 to the tip 40. The threaded portion 42 of shaft 38 includes a compression thread which has a large thread depth between 0.1 mm and 3.0 mm, in particular between 0.2 mm and 2.0 mm, and a long thread pitch between 0.1 mm and 5.0 mm, in particular between 0.25 mm and 3.0 mm. As shown in FIG. 3, the thread 42 of shaft 38 has a smaller core or root diameter than the non-threaded portion 44. However, the outer or major diameter of the threaded portion 42 is greater than the diameter of the non-threaded portion 44.

FIG. 4 illustrates a side view of an embodiment of a bone screw 46 which is a combination of the screw head 14 having the thread configuration of bone screw 30 shown in FIG. 2 and a shaft 38 formed as the shaft of bone screw 36 shown in FIG. 3.

FIG. 5 illustrates in schematic form a detailed view of the thread configuration of an exemplary screw head 14 shown in FIGS. 2 and 4 to illustrate certain geometrical features of the bone screw embodiments. In this configuration, the peaks 28 of the thread 32 have a curved shape and are separated from each other by valleys 34 having a planar profile in cross section. As shown in FIG. 5, each curved peak 28 forms an arc segment 48. The arc segment can be a segment of a circle (as shown), of an ellipse or of any other curved structure.

The arc segment 48 is defined by a radius of curvature r and a centre point m. This radius of curvature of the arc segment is between 0.05 mm and 3.0 mm, in particular between 0.1 mm and 1.0 mm. Moreover, each arc segment 48 has an angular range w which is between 30° and 200°, in particular between 45° and 180°. As illustrated in FIG. 5, the arc segment 48 is not semicircular (i.e. w<180°) and the peak 28 of the arc segment 48 is defined by an angle k between a plane p including the core diameter of the thread 32 of the screw head 14 and a tangent t to the arc segment 48 where it intersects the core. This angle k can be between −10° and 90°, in particular between 0° and 50°. Further, the more strongly inclined portion 50 of the arc segment 48 can be defined by curved flanks 50. Each curved flank 50 connects the valley 34 with the top of peak 28. It should be noted that the flanks 50 may generally have a different curvature than the arc segments 48 defining the peaks 28. Moreover, as shown in FIG. 5, each curved peak 28 can be defined by a height h which extends from a plane defined by the core of the screw head 14 to the top of peak 28. This height h of the peak 28 can be between 0.1 mm and 3.0 mm, in particular between 0.15 mm and 1.5 mm.

FIGS. 6 and 7 show a detailed cross-sectional view of screw head 14. The screw head 14 as illustrated in FIG. 6 has the thread configuration of thread 16 according to the screw head shown in FIGS. 1 and 3, wherein the curved peaks 28 are provided immediately adjacent to each other on the outer surface of head 14. FIG. 7 illustrates the thread configuration of thread 32 according to the screw head shown in FIGS. 2 and 4, wherein the curved peaks 28 are separated from each other by valleys 34 having a planar profile in cross section. As seen from FIGS. 6 and 7, the screw head 14 tapers toward the screw shaft, and has therefore a conical shape. The conical shape of screw head 14 is defined by a cone angle u which is between 10° and 179°. In the present embodiments, the cone angle u is 20° or 30°.

Moreover, the screw head 14 includes a tool holder portion 52 for receiving a tool like a screw driver or the like. The tool holder portion 52 may be formed by a recess 52 which is arranged within the screw head 14 and symmetrically to a central axis 54 of the bone screw. An opening 56 of the recess 52 is arranged in the top surface of the screw head 14. In a cross-sectional view in a plane perpendicular to the central axis 54 of the bone screw, the profile of the tool holder portion 52 forms a star-shaped pattern with rounded peaks and edges, like a torx socket. This tool holder socket 52 has a tapering upper portion 58 with an opening angle o. The opening angle o of this phase 58 of the tool holder socket 52 is between 10° and 179°, in particular 120°.

Figure 8:
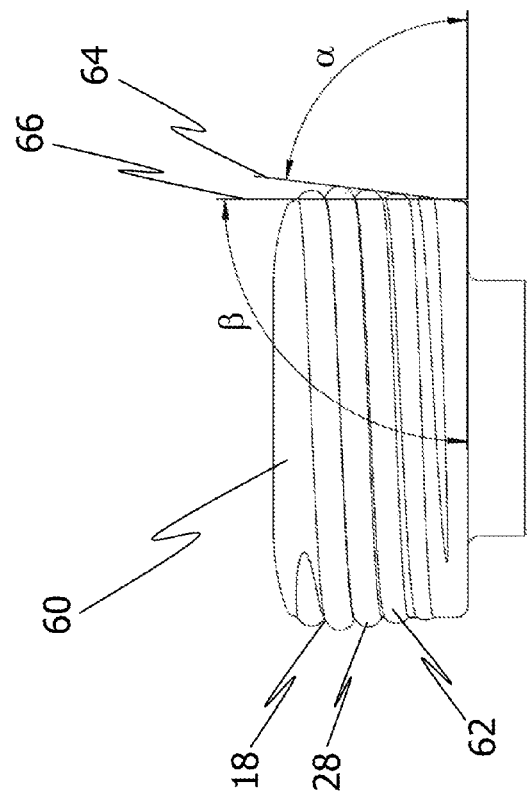
FIG. 8 is a detailed view of another screw head embodiment.

FIG. 8 shows a side view of a further embodiment of a screw head 60 having a thread 62 with peaks 28. The screw head 60 has a constant core diameter and thus forms a cylinder. Further, as shown in FIG. 8, the outer diameter of the thread 62 of the head 60 gradually tapers. Thus, the thread 62 forms an envelope which has a conical shape defined by an angle α between the outer surface of the envelope 64 and a plane including the core diameter of the head 60 and perpendicular to the central axis 54 of the bone screw. This angle α can be between 10° and 89°, and is in particular 70° to 85°. Further, an angle β between a plane 66 defined by the core of the head 60 and the plane perpendicular to the central axis 54 of the bone screw is 90°.

Figure 9:
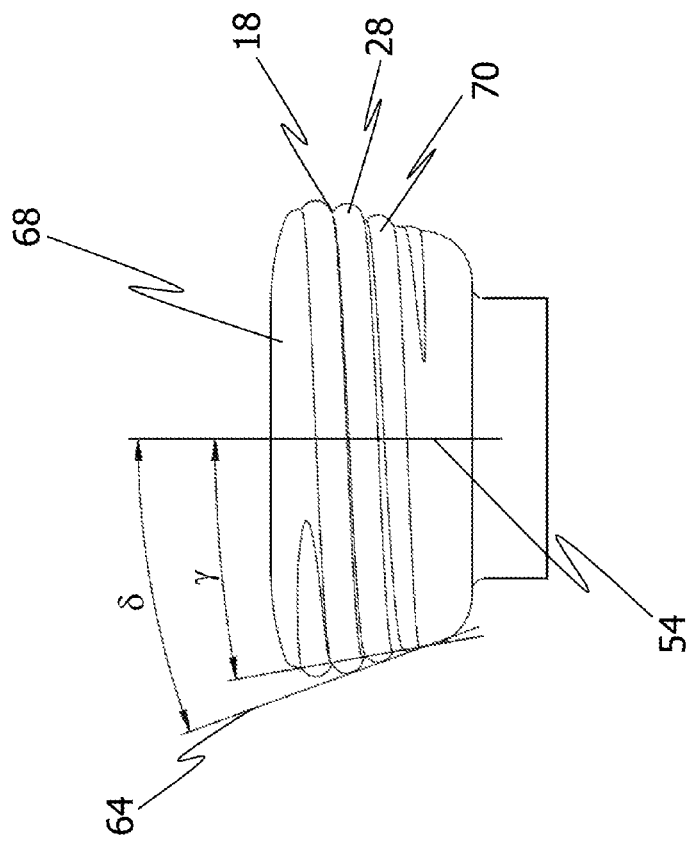
FIG. 9 is a detailed view of another screw head embodiment.

FIG. 9 illustrates a side view of a screw head 68 having a thread 70 with peaks 28. The difference between screw head 60 shown in FIG. 8 and screw head 68 shown in FIG. 9 is the fact that the core of the head 68 has a conical shape defined by an angle γ between the central axis 54 of the screw and a plane defined by the conical core of the screw head 68. This angle γ can be between 1° and 50°, and is approximately 10° in the embodiment of FIG. 9. Further, the outer diameter of the thread 70 of the head 68 gradually tapers and defines the envelope 64. The envelope 64 also tapers towards the shaft of the bone screw, wherein an angle δ is defined between an outer surface of envelope 64 and the central axis 54 of the bone screw. This angle δ can be between 1° and 50°, and is approximately 20° in the embodiment of FIG. 9.

Figure 10:
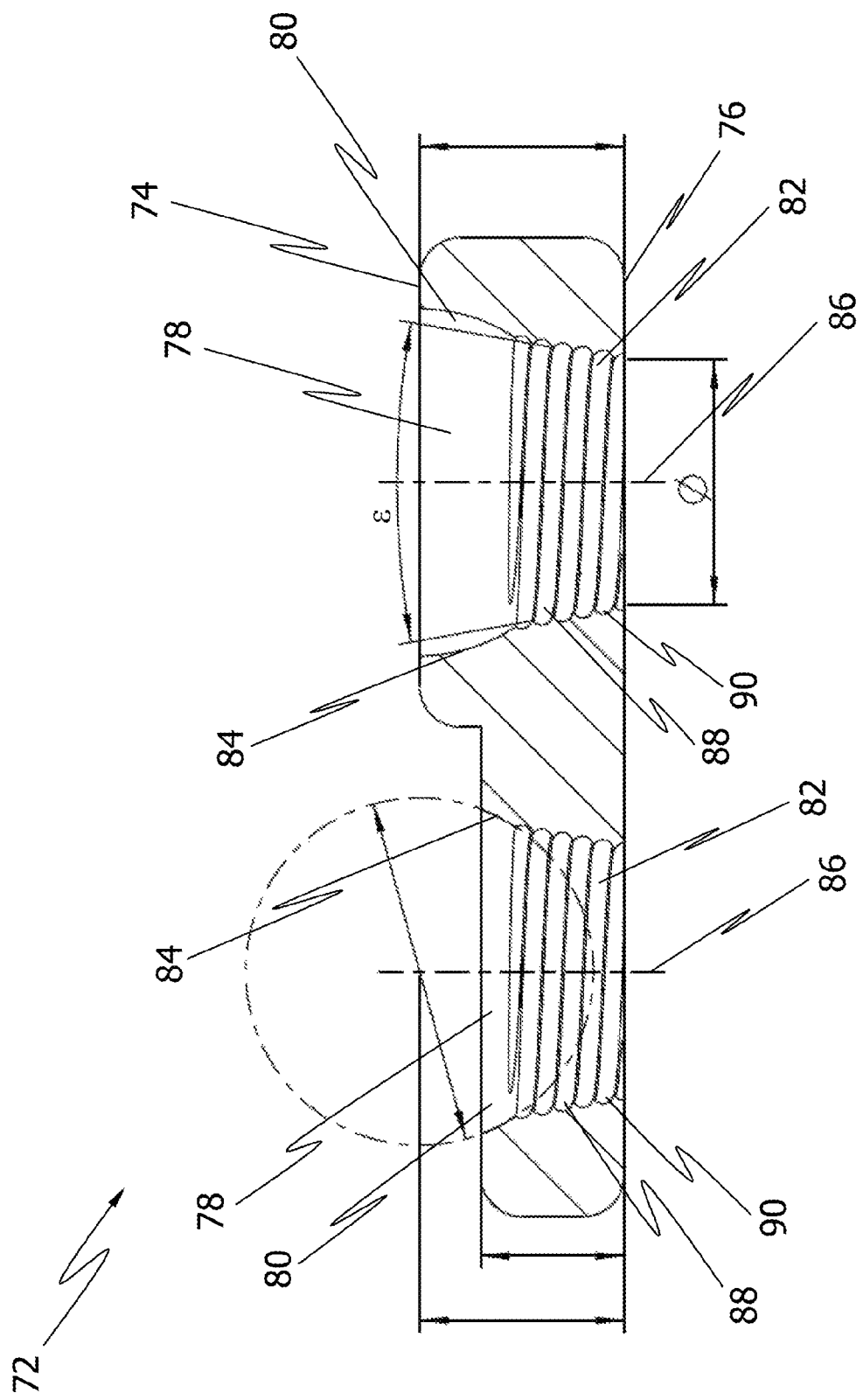
FIG. 10 is a cross-sectional view of a dummy implant embodiment.

FIG. 10 illustrates in a cross-sectional view an embodiment of an implant in the form of a dummy bone plate 72 that can be adapted as needed (e.g., in terms of shape, thickness, etc.) for use in orthopedic surgery for fixation of bone. The bone plate 72 has an upper surface 74 and a lower surface 76. Further, as shown in FIG. 10, the bone plate 72 comprises two holes 78 extending through the upper surface 74 and the lower surface 76 for receiving a bone fastener (e.g., a bone screw as described above and shown in FIGS. 1 to 9). The bone plate 72 has a varying thickness along its entire length.

Each hole 78 includes an (optional) upper portion 80 and a lower threaded portion 82 configured to mate with the thread of the head of the bone fastener. The upper portion 80 of each hole 78 has an inward taper 84 generally having a conical or curved (e.g., spherical) shape. The curved or spherical shape of the inward taper 84 of the upper portion 80 can be defined by an segment of a circle or ellipse in cross section with a center point arranged on a position along a central axis 86 of the hole 78.

The lower portion 82 of each hole 78 tapers toward the lower surface 76 of the bone plate 72. The taper of the threaded portion 82 is defined by a cone angle ε which is between 1° and 179°, in particular between 10° and 120°, and more particularly approximately 20° in the embodiment of FIG. 10. As shown in FIG. 10, the lower threaded portion 82 comprises a thread 88 with curved valleys 90 which are provided immediately adjacent to each other. Further, the thread 88 of hole 78 is a multiple thread (a double thread). In one implementation, an implant system comprises at least the bone plate 72 with the double thread 88 as well as a bone fastening element comprising a head with a single thread (such as any of the bone screws of FIG. 2, 4, 7 or 9).

FIGS. 11 and 11A show another embodiment of an implant in form of a dummy bone plate 92 having several plate holes 78 as illustrated in FIG. 10 with a head portion 94 and a shaft portion 96. As shown in the side view of the bone plate 92 in FIG. 11, the head portion 94 has a smaller thickness than the shaft portion 96. Further, as shown in FIG. 11A, the bone plate 92 has several screw holes 78 arranged along the plate and oblique relative to the upper surface 74 of the bone plate 92. The bone plate 92 can be adapted as needed (e.g., in terms of shape, thickness, etc.) for use in orthopedic surgery for fixation of bone.

FIG. 12 illustrates a cross-sectional view A-A of bone plate 92 along the intersection line shown in FIG. 11. It can be seen from FIG. 12 that each hole 78 of the bone plate 92 can have a different angular orientation with respect to the bone plate 92. This angular orientation is defined by the central axis 86 of the hole 78 and a vertical axis 98 of the bone plate 92. Therefore, as shown in FIG. 12, the central axis 86 of the hole 78 can be oblique relative to the vertical axis 98 of the bone plate 92, wherein angles a, b, c, d, e, f are defined between the central axis 86 and the vertical axis 98. These angles can be between 0° and 60°.

An implant system comprising an implant and at least one bone fastener as described above can be used in orthopedic surgery for fixation of bone. The bone fasteners and implants can generally be made of stainless steel, titanium or any other biocompatible material. While the head of the bone fastener includes thread peaks having a rounded shape, the shaft of the bone fastener can be adapted to different applications and may thus be threaded or un-threaded. In the case of a threaded shaft, the thread peaks of the shaft may generally not be rounded. Moreover, in the case a hole of the implant is provided with a thread, this thread may be rounded or non-rounded.

While the bone plate holes shown herein are circular, they could be elongated and be partially threaded as shown in U.S. Pat. No. 5,709,686 ("the '686 Patent"). The threads shown in the '686 Patent would be replaced by the curved profile threads described herein.

The curved peaks of the thread of the head of the bone fastener improve the engagement of the thread in an implant hole. Moreover, tilting and jamming is avoided or at least reduced during the screwing-in operation of the threaded bone fastener head into the implant hole. Thereby, the thread of the bone fastener head and the optionally threaded portion of the implant hole are not damaged (and the patient is not harmed by thread parts which may result from this damage). Further, splinters from the bone drilling as well as further materials like parts of human tissue adhering to the threads have less detrimental effects due to the rounded peaks.

While the above embodiments have primarily been described in relation to bone screws and bone plates, it will be readily apparent that the techniques presented herein can also be implemented in combination with other types of bone fasteners (such as bone pegs having rod-like or pin-like shafts, wire-like bone fasteners such as Kirschner wires, etc.) as well as other types of implants (such as bone distractors). Accordingly, the present disclosure is not limited to any type of bone fastener or any type of implant.

The features described in the above description taken in conjunction with the accompanying drawings can be readily combined to result in different embodiments. It will thus be apparent that the disclosure described above may be varied in many ways. Such variations are not to be regarded as a departure from the scope of the disclosure, and all such modifications as would be apparent to one skilled in the art are intended to be included within the scope of the following claims.

The invention claimed is:

1. A bone fastener for use in orthopaedic surgery for fixing an implant to bone, comprising:
   a shaft having a first diameter configured to engage bone, the shaft having a first thread formed thereon;
   a head adjacent the shaft, the head having a second diameter larger than the first diameter;
   a second thread formed on at least a portion of the head, the second thread having a cross sectional profile along a longitudinal axis of the head including peaks located between first and second flanks, wherein the second thread has a curved shape along the profile with a constant radius of curvature in the form of an arc segment of a circle from the first flank to the peak to the second flank with a center point located within the second diameter of the head;
   wherein the first and second flanks of the second thread is flanked by planar valleys.

2. The bone fastener of claim 1, wherein the first thread is separated from the head by a non-threaded portion of the shaft.

3. The bone fastener of claim 1, wherein each of the first and second flanks have a radius different than a radius of the curved shape of the second thread located between the first and second flanks.

4. The bone fastener of claim 3, wherein the angular range of the arc segment is between 30° and 200°.

5. The bone fastener of claim 1, wherein the head has a constant diameter.

6. The bone fastener of claim 1, wherein the head has a conical or curved shape.

7. The bone fastener of claim 1, further comprising a recess in the head to receive a tool to rotate the bone fastener.

8. The bone fastener of claim 1, wherein the first flank and the second flank have equal radii.

9. The bone fastener of claim 1, wherein a radius of curvature of the arc segment is between 0.05 mm and 3.0 mm.

10. An implant system for fixation of bone comprising:
    an implant having an upper surface, a lower surface, and at least one hole extending through the implant; and
    a bone fastener comprising a shaft configured to engage bone, the shaft having a first diameter and a first thread formed thereon, a head adjacent the shaft, the head having a second diameter larger than the first diameter, a second thread formed on at least a portion of the head, the second thread having a cross sectional profile along a longitudinal axis of the head including peaks located between first and second flanks, wherein the second thread has a curved shape along the profile with a constant radius of curvature in the form of an arc segment of a circle from the first flank to the peak to the second flank with a center point located within the second diameter of the head;
    wherein the first and second flanks of the second thread is flanked by planar valleys.

11. The implant system of claim 10, wherein the at least one hole comprises a threaded portion to mate with the second thread of the head of the bone fastener.

12. The implant system of claim 10, wherein each of the first and second flanks have a radius different than a radius of the curved shape of the second thread located between the first and second flanks.

13. The implant system of claim 10, wherein the at least one hole has a central axis which is oblique relative to a vertical axis of the implant.

14. The implant system of claim 10, wherein the at least one hole includes an upper unthreaded portion and a lower threaded portion configured to mate with the second thread of the head of the bone fastener.

15. The implant system according of 14, wherein the threaded portion of the at least one hole tapers inwardly toward the lower surface of the implant.

16. A bone fastener for use in orthopaedic surgery for fixing an implant to bone, comprising:
- a shaft having a first core diameter, the shaft configured to engage bone; and
- a head formed on the shaft, the head having a second core diameter larger than the first core diameter of the shaft, the second core diameter being the largest core diameter of the bone fastener, the head having a thread on at least a portion of an outer surface thereon and at least on the second core diameter, the thread being formed to correspond to a thread of the implant,
- wherein the entire thread has a profile in longitudinal cross section along a longitudinal axis of the head including peaks located between first and second flanks,
- wherein the second thread has a curved shape along the profile with a constant radius of curvature in the form of an arc segment of a circle from the first flank to the peak to the second flank with a center point located within the second core diameter of the head, and
- wherein the first and second flanks of the thread is flanked by planar valleys.

17. The bone fastener of claim 16, wherein the constant radius of curvature extends along substantially the entire profile.

18. The bone fastener of claim 16, wherein each of the first and second flanks have a radius different than a radius of the curved shape of the second thread located between the first and second flanks.

19. The bone fastener of claim 16, wherein an angular range of the arc segment is between 30° and 200°.

* * * * *